United States Patent [19]
Fukuda et al.

[11] Patent Number: 6,136,977
[45] Date of Patent: Oct. 24, 2000

[54] PROCESSES FOR PRODUCING PHENOXY PROPIONIC ACID DERIVATIVES

[75] Inventors: Kenzo Fukuda; Masataka Hatanaka; Takahiro Makabe; Kenichi Ishii, all of Onoda, Japan

[73] Assignee: Nissan Chemical Industries, Ltd., Tokyo, Japan

[21] Appl. No.: 09/147,327

[22] PCT Filed: May 21, 1997

[86] PCT No.: PCT/JP97/01711

§ 371 Date: Dec. 3, 1998

§ 102(e) Date: Dec. 3, 1998

[87] PCT Pub. No.: WO97/46538

PCT Pub. Date: Dec. 11, 1997

[30] Foreign Application Priority Data

Jun. 3, 1996 [JP] Japan ..................................... 8-140113
Apr. 25, 1997 [JP] Japan ..................................... 9-108847

[51] Int. Cl.$^7$ .......................... A01N 43/60; C07D 241/44
[52] U.S. Cl. .............................................................. 544/354
[58] Field of Search ............................................... 544/354

[56] References Cited

FOREIGN PATENT DOCUMENTS 23785 10/1988 European Pat. Off. .
288275 10/1988 European Pat. Off. .

*Primary Examiner*—Mukund J. Shah
*Assistant Examiner*—Sudhaker B. Patel
*Attorney, Agent, or Firm*—Oblon, Spivak, McClelland, Maier & Neustadt, P.C.

[57] ABSTRACT

The present invention relates to processes for producing D(+)-2-[4-(6-chloro-2-quinoxalyloxy)phenoxy]propionic acid and ester derivatives thereof and which can be used as selective herbicides for foliage treatment for controlling gramineous weeds against broad leaf crop plants.

27 Claims, No Drawings

PROCESSES FOR PRODUCING PHENOXY PROPIONIC ACID DERIVATIVES

This application is a 371 of PCT/JP97/01711, filed May 21, 1997.

TECHNICAL FIELD

The present invention relates to processes for producing D(+)-2-[4-(6-chloro-2-quinoxalyloxy)phenoxy]propionic acid and D(+)-2-[4-(6-chloro-2-quinoxalyloxy)phenoxy] propionic acid esters derived from the propionic acid. The esters are useful as selective herbicides for foliage treatment for controlling gramineous weeds against broad leaf crop plants.

BACKGROUND ART

Nippon Kagaku Kaishi, p. 253, (1991) discloses a process for producing ethyl D(+)-2-[4-(6-chloro-2-quinoxalyloxy) phenoxy]propionate, which comprises reacting an alkali metal salt of 4-(6-chloro-2-quinoxalyloxy)phenol with ethyl L-2-chloropropionate. JP-A-7-278047 discloses a process for producing D(+)-2-[4-(6-chloro-2-quinoxalyloxy) phenoxy]propionic acid, which comprises reacting an alkali metal salt and/or an alkaline earth metal salt of 4-(6-chloro-2-quinozalyloxy)phenol with an alkaline earth metal salt of L-2-chloropropionic acid. Further, U.S. Pat. No. 4,687,849 discloses a process for producing 2-isopropylidene aminoxyethyl D(+)-2-[4-(6-chloro-2-quinoxalyloxy)phenoxy] propionate, which comprises reacting 2-isopropylidene aminoxyethyl L(−)-2-(p-toluenesulfonyl)oxypropionate with 4-(6-chloro-2-quinoxalyloxy)phenol, a process for producing 2-isopropylidene aminoxyethyl D(+)-2-[4-(6-chloro-2-quinoxalyloxy)phenoxy]propionate, which comprises reacting 2-isopropylidene aminoxyethyl D(+)-2-(4-hydroxyphenoxy)propionate with 2,6-dichloroquinoxaline, and a process for producing 2-isopropylidene aminoxyethyl D(+)-2-[4-(6-chloro-2-quinoxalyloxy)phenoxy]propionate, which comprises reacting D(+)-2-[4-(6-chloro-2-quinoxalyloxy)phenoxy]propionic acid chloride with 2-isopropylidene aminoxyethanol. Further, JP-B-7-25753 discloses a process for producing tetrahydrofurfuryl 2-[4-(6-chloro-2-quinoxalyloxy)phenoxy]propionate, which comprises reacting tetrahydrofurfuryl 2-bromopropionate with 2-(4-hydroxyphenoxy)-6-chloroquinoxaline, and JP-A-4-295469 discloses a process for producing 2-isopropylidene aminoxyethyl D(+)-2-[4-(6-chloro-2-quinoxalyloxy)phenoxy]propionate, which comprises an ester exchange reaction of ethyl D(+)-2-[4-(6-chloro-2-quinoxalyloxy)phenoxy]propionate obtained by a reaction of 2,6-dichloroquinoxaline with ethyl D(+)-2-(4-hydroxypheoxy)propionate.

The process disclosed in Nippon Kagaku Kaishi, p. 253 (1991) is not necessarily industrially satisfactory for producing a product of high optical purity.

Whereas, JP-A-7-278047 discloses that in the reaction of an alkali metal salt of 4-(6-chloro-2-quinoxalyloxy)phenol with an alkali metal salt of L-2-chloropropionic acid, the reaction is terminated at a conversion of about 50% due to a side-reaction, and the yield is very low. The same publication also discloses that a barium salt is particularly preferred as the alkali salt and/or the alkaline earth metal salt. However, if the barium salt is used, there is a problem that a large amount of barium-related compounds as typical by-products is formed, and it has been desired to develop a more efficient production process.

DISCLOSURE OF THE INVENTION

The present inventors have conducted an extensive study to solve the above-mentioned problems and as a result, have accomplished the present invention. Namely, the present invention provides a process for producing D(+)-2-[4-(6-chloro-2-quinoxalyloxy)phenoxy]propionic acid (hereinafter referred to as compound (III)), which comprises reacting 4-(6-chloro-2-quinoxalyloxy)phenol (hereinafter referred to as compound (I)) or its alkali metal salt with L-2-chloropropionic acid (hereinafter referred to as compound (II)) or its alkali metal salt in an aromatic hydrocarbon solvent in the presence of an aprotic polar solvent and, if necessary, an alkali metal hydroxide, if necessary while carrying out azeotropic dehydration, to obtain an alkali metal salt of D(+)-2-[4-(6-chloro-2-quinoxalyloxy) phenoxy]propionic acid, and treating it with an acid.

By the process of the present invention, compound (III) can be produced at a high conversion in good yield without deterioration of the optical purity.

Further, in the process of the present invention, an alkali metal salt of D-2-chloropropionic acid may be employed instead of the alkali metal salt of L-2-chloropropionic acid to obtain L(−)-2-[4-(6-chloro-2-quinoxalyloxy)phenoxy] propionic acid, which can be inverted to produce D(+)-2-[4-(6-chloro-2-quinoxalyloxy)phenoxy]propionic acid.

Further, compound (III) produced by the process of the present invention can be esterified to produce a heteroaryloxy propionic acid type herbicide, such as ethyl D(+)-2-[4-(6-chloro-2-quinoxalyloxy)phenoxy]propionate, tetrahydrofurfuryl D(+)-2-[4-(6-chloro-2-quinoxalyloxy)phenoxy] propionate, or isopropylidene aminoxyethyl D(+)-2-[4-(6-chloro-2-quinoxalyloxy)phenoxy]propionate.

For example, it is possible to produce ethyl D(+)-2-[4-(6-chloro-2-quinoxalyloxy)phenoxy]propionate by reacting compound (III) with diethyl sulfate in the presence of a tertiary amine and a base.

The present invention is also useful for producing other heteroaryloxy propionic acid type herbicides such as fluazifop-p-butyl (common name) and fenoxaprop-p-ethyl (common name).

Now, the present invention will be described in detail with reference to the preferred embodiments.

The alkali metal salt of compound (I) may, for example, be a potassium salt or a sodium salt.

The alkali metal salt of compound (I) can be produced from compound (I) and an alkali metal compound.

The alkali metal compound may, for example, be a metal such as sodium or potassium, an alkali metal hydride such as sodium hydride or potassium hydride, or an alkali metal hydroxide such as sodium hydroxide or potassium hydroxide. In view of the reactivity and economical efficiency, sodium hydroxide is preferred.

The amount of the alkali metal compound is usually within a range of from 1 to 10 mols, preferably from 1 to 2 mols, per mol of compound (I).

Further, the alkali metal salt of compound (I) can also be prepared from 2,6-dichloroquinoxaline (hereinafter referred to as compound (IV)), hydroquinone and an alkali metal compound.

The alkali metal compound may, for example, be a metal such as sodium or potassium, an alkali metal hydride such as sodium hydride or potassium hydride, or an alkali metal hydroxide such as sodium hydroxide or potassium hydroxide. In view of the reactivity and economical efficiency, sodium hydroxide is preferred.

With respect to the amount of the alkali metal compound, for example, in the case of sodium hydroxide, the amount is usually within a range of from 1.8 to 3 mols, preferably from 2.0 to 2.5 mols, per mol of compound (IV).

The amount of hydroquinone is usually within a range of from 1 to 1.5 mols, preferably from 1.00 to 1.05 mols, per mol of compound (IV).

For the production of compound (I) or its alkali metal salt, an organic solvent may also be used, as the case requires. The organic solvent is preferably an aprotic polar solvent, more preferably N,N-dimethylformamide. Further, a solvent mixture of N,N-dimethylformamide with an aromatic hydrocarbon such as benzene or toluene, may also be employed.

The reaction temperature is usually within a range of from 20 to 120° C., preferably from 50 to 70° C.

When water is formed during the production of the alkali metal salt of compound (I), formed water may be removed so that the reaction proceeds smoothly.

The alkali metal salt of compound (II) may, for example, be a potassium salt or a sodium salt.

The alkali metal salt of compound (II) can be produced from compound (II) and an alkali metal compound.

The alkali metal compound may, for example, be a metal such as sodium or potassium, an alkali metal hydride such as sodium hydride or potassium hydride, an alkali metal hydroxide such as sodium hydroxide or potassium hydroxide, an alkali metal carbonate such as sodium carbonate or potassium carbonate, or an alkali metal hydrogencarbonate such as sodium hydrogencarbonate or potassium hydrogencarbonate. In view of the reactivity and economical efficiency, sodium carbonate is preferred.

The amount of the alkali metal compound is usually within a range of from 1 to 10 mols, preferably from 1 to 2 mols, per mol of compound (II).

For the production of the alkali metal salt of compound (II), an organic solvent may be used, as the case requires. The organic solvent is not particularly limited so long as it is inert to the reaction. For example, an aromatic hydrocarbon solvent such as benzene or toluene is preferred.

The reaction temperature is usually within a range of from 20 to 120° C., preferably from 50 to 70° C.

When water is formed during the production of the alkali metal salt of compound (II), formed water may be removed so that the reaction proceeds smoothly.

The method for reacting the alkali metal salt of compound (I) with the alkali metal salt of compound (II) may, for example, be a method in which the alkali metal salt of compound (I) and the alkali metal salt of compound (II) are separately produced and reacted, a method wherein the compound (I) is reacted with compound (II) in the presence of an alkali metal compound, or a method wherein the alkali metal salt of compound (I) is reacted with compound (II) in the presence of an alkali metal compound.

Otherwise, it is possible to employ a method of adding the alkali metal salt of compound (II) to the reaction solution at the time of the production of the alkali metal salt of compound (I), or adding an alkali metal hydroxide and compound (II) to the reaction solution at the time of the production of the alkali metal salt of compound (I).

The amount of compound (II) or its alkali metal salt is usually within a range of from 1 to 1.5 mols, preferably from 1.1 to 1.3 mols, per mol of compound (I) or its alkali metal salt.

The solvent to be used for the reaction of compound (I) or its alkali metal salt with compound (II) or its alkali metal salt, is preferably an aromatic hydrocarbon solvent containing an aprotic polar solvent. The aprotic polar solvent may, for example, be N,N-dimethylformamide, N,N-dimethylacetamide, N-methylpyrrolidone or 1,3-dimethyl-2-imidazolidinone. Particularly preferred is N,N-dimethylformamide. The aromatic hydrocarbon solvent may, for example, be toluene or benzene, and particularly preferred is toluene. Further, a solvent mixture of the above-mentioned solvents used for the production of the respective compounds, may also be used.

The organic solvent may be used in a large amount without any particular problem. However, taking the economical efficiency and the reactivity into consideration, it is preferably used in an amount of from 8 to 9 parts by weight per part by weight of compound (I).

The reaction temperature is usually within a range of from 20 to 120° C., preferably from 50 to 70° C.

When water is formed in the reaction of compound (I) or its alkali metal salt with compound (II) or its alkali metal salt, formed water may be removed so that the reaction proceeds smoothly.

By the reaction of compound (I) or its alkali metal salt with compound (II) or its alkali metal salt, an alkali metal salt of compound (III) will be formed. By subjecting the reaction solution containing this alkali metal salt of compound (III) to acid treatment, compound (III) can be produced.

The acid may, for example, be a mineral acid such as hydrochloric acid, sulfuric acid or nitric acid, or an organic acid such as p-toluenesulfonic acid, and such an acid may be used as it is or in the form of an aqueous acid solution.

The acid is used in an amount sufficient to acidify the reaction mixture.

The temperature for the acid treatment is usually within a range of from 0 to 100° C., preferably at most 60° C.

Compound (III) may be further purified by means of alkali and acid treatment, extraction, washing, recrystallization or chromatography, as the case requires.

Compound (III) obtained by the present invention, can be esterified with an alcohol, an alkyl halide or a dialkyl sulfate.

The esterification method may, for example, be a method wherein compound (III) is converted to an acid chloride or acid anhydride and then reacted with an alcohol, a method wherein compound (III) is reacted with an alcohol in the presence of an acid catalyst such as sulfuric acid, a method wherein compound (III) is reacted with an alcohol in the presence of a dehydrating agent such as dicyclohexylcarbodiimide, a method wherein compound (III) is reacted with various esterification agents, or an ester exchange reaction.

The esterification agents include, in addition to those mentioned above, a methanesulfonic acid ester produced from an alcohol and methanesulfonyl chloride, a 4-toluenesulfonic acid ester produced from an alcohol and 4-toluenesulfonyl chloride, and a diazoalkane.

BEST MODE FOR CARRYING OUT THE INVENTION

Now, the present invention will be described in further detail with reference to Examples. However, it should be understood that the present invention is by no means restricted to such specific Examples.

EXAMPLE 1

Into a reaction flask flushed with nitrogen, 59.7 g (0.3 mol) of 2,6-dichloroquinoxaline, 33.0 g (0.3 mol) of hydroquinone, 24.2 g (0.6 mol) of sodium hydroxide, 120 g of toluene and 180 g of N,N-dimethylformamide were charged, and the temperature was raised from 40° C. to 80° C. to form a sodium salt of 4-(6-chloro-2-quinoxalyloxy) phenol. Into a separate reaction flask flushed with nitrogen, 35.8 g (0.33 mol) of L-2-chloropropionic acid (optical purity: 96%ee), 17.5 g (0.165 mol) of sodium carbonate and 240 g of toluene were charged and reacted by a conventional method at 50° C. to obtain a reaction solution in which a sodium salt of L-2-chloropropionic acid was formed. To this reaction mixture, the reaction mixture of the sodium salt of 4-(6-chloro-2-quinoxalyloxy)phenol was added together with 120 g of toluene. To this mixture, 3.6 g (0.09 mol) of sodium hydroxide was added, and the mixture was reacted for 4 hours while azeotropically dehydrating it at 60° C. under reduced pressure. Then, while maintaining the temperature at 60° C., 240 ml of water was added, and the toluene layer was separated and removed. Then, the aqueous layer was again washed with 240 ml of toluene. Again, 240 ml of toluene was added thereto, and 35% hydrochloric acid was added to bring the pH to 3, followed by liquid separation. The obtained toluene layer was quantitatively analyzed by high performance liquid chromatography to confirm formation of 98.3 g (yield: 95%) of D(+)-2-[4-(6-chloro-2-quinoxalyloxy)phenoxy]propionic acid. The optical purity was 96%ee.

EXAMPLE 2

Into a reaction flask flushed with nitrogen, 59.7 g (0.3 mol) of 2,6-dichloroquinoxaline, 33.0 g (0.3 mol) of hydroquinone, 24.9 g (0.57 mol) of sodium hydroxide and 300 g of N,N-dimethylformamide were charged and reacted at 35° C. for 3 hours under reduced pressure (20 mmHg). Then, the temperature was gradually raised to 75° C., and the mixture was reacted at that temperature for 3 hours under reduced pressure (70 mmHg). Then, 180 g of N,N-dimethylformamide was distilled off, and 480 g of toluene was added thereto. Then, 21.6 g (0.54 mol) of sodium hydroxide was added thereto, and 42.3 g (0.39 mol) of L-2-chloropropionic acid (optical purity: 96%ee) was added dropwise thereto over a period of 1 hour at 50° C. After completion of the dropwise addition, the temperature was raised to 60° C., and the mixture was reacted for 4 hours while azeotropically dehydrating it under reduced pressure. Then, while maintaining the temperature at 60° C., 240 ml of water was added, whereupon the toluene layer was separated and removed. The aqueous layer was washed with 240 ml of toluene. Then, to the aqueous layer, 240 ml of toluene was added, and the aqueous layer was adjusted to pH 3 with 35% hydrochloric acid. Then, the aqueous layer was separated and removed. The obtained toluene layer was quantitatively analyzed by high performance liquid chromatography to confirm formation of 96.2 g (yield: 93%) of D(+)-2-[4-(6-chloro-2-quinoxalyloxy)phenoxy]propionic acid. The optical purity was 96%ee.

EXAMPLE 3

27.4 g (0.100 mol) of 4-(6-chloro-2-quinoxalyloxy) phenol, 40 g of N,N-dimethylformamide and 120 g of toluene were charged into a flask, and 9.0 g (0.23 mol) of sodium hydroxide was added thereto. The mixture was reacted at 40° C. for 1 hour. Then, 14.2 g (0.12 mol) of L-2-chloropropionic acid was added thereto at 50° C. Then, the temperature was raised to 60° C., and the mixture was reacted for 4 hours while azeotropically dehydrating it under reduced pressure. Then, while maintaining the temperature at 60° C., 80 ml of water was added thereto, and the toluene layer was separated and removed. Then, the aqueous layer was further washed with 80 ml of toluene. To the aqueous layer, 80 ml of toluene was added, and the aqueous layer was adjusted to pH 3 with 35% hydrochloric acid. Then, the aqueous layer was separated and removed. The obtained toluene layer was quantitatively analyzed by high performance liquid chromatography to confirm formation of 32.8 g (yield: 95%) of D(+)-2-[4-(6-chloro-2-quinoxalyloxy) phenoxy]propionic acid. The optical purity was 96%ee.

EXAMPLE 4

3.6 g of water, 2.64 g (0.014 mol) of tributylamine and 70.9 g (0.51 mol) of potassium carbonate were added at 60° C. to a toluene solution containing 98.3 g (0.29 mol) of D(+)-2-[4-(6-chloro-2-quinoxalyloxy)phenoxy]propionic acid obtained in Example 1, and the mixture was stirred for 30 minutes. Then, 57.1 g (0.37 mol) of diethyl sulfate was added dropwise, and the mixture was reacted for 5 hours. Then, 147 g of water was added thereto, and the aqueous layer was separated and removed. The toluene layer was washed twice with 147 g of water and then the toluene layer was distilled to obtain 106.3 g (yield: 95%) of ethyl D(+)-2-[4-(6-chloro-2-quinoxalyloxy)phenoxy]propionate. The optical purity was 96%ee.

EXAMPLE 5

6.9 g (0.02 mol) of D(+)-2-[4-(6-chloro-2-quinoxalyloxy) phenoxy]propionic acid, 15.9 g of toluene and 4.64 g of N,N-dimethylformamide were charged into a flask, and the temperature was raised to 60° C. Then, 4.14 g (0.04 mol) of thionyl chloride was added dropwise thereto at a temperature of from 60 to 70° C. Then, the mixture was reacted at 70° C. for 4 hours to form D(+)-2-[4-(6-chloro-2-quinoxalyloxy)phenoxy]propionic acid chloride. After cooling, excess thionyl chloride was distilled off under reduced pressure, and this reaction solution was added dropwise at a temperature of not higher than 30° C. to a mixed liquid comprising 8.9 g (0.10 mol) of tetrahydrofurfuryl alcohol and 4.12 g (0.06 mol) of pyridine, followed by stirring at room temperature for 2 hours. Then, this reaction solution was washed three times with a 1% sodium hydroxide aqueous solution and twice with 1% hydrochloric acid and then three times with water. Then, toluene was distilled off under reduced pressure to obtain 6.8 g (yield: 79%) of tetrahydrofurfuryl D(+)-2-[4-(6-chloro-2-quinoxalyloxy) phenoxy]propionate. The optical purity was 96%ee.

EXAMPLE 6

6.9 g (0.02 mol) of D(+)-2-[4-(6-chloro-2-quinoxalyloxy) phenoxy]propionic acid, 15.9 g of toluene and 4.64 g of N,N-dimethylformamide were charged into a flask, and 4.14 g (0.04 mol) of thionyl chloride was added dropwise thereto at 40° C. Then, the temperature was raised, and the mixture was reacted at 60° C. for 3 hours to form D(+)-2-[4-(6-chloro-2-quinoxalyloxy)phenoxy]propionic acid chloride. After cooling, excess thionyl chloride was distilled off under reduced pressure. This reaction solution was added dropwise at a temperature of not higher than 30° C. to a mixed liquid comprising 11.7 g (0.10 mol) of isopropylidene aminoxyethanol and 4.12 g (0.06 mol) of pyridine, followed by stirring at room temperature for 2 hours. Then, this reaction solution was washed three times with a 1% sodium hydroxide aqueous solution, twice with 1% hydrochloric acid and then three times with water. Then, toluene was distilled off under reduced pressure to obtain 6.8 g (yield: 77%) of isopropylidene aminoxyethyl D(+)-2-[4-(6-chloro-2-quinoxalyloxy)phenoxy]propionate. The optical purity was 96%ee.

EXAMPLE 7

3.5 g (0.01 mol) of D(+)-2-[4-(6-chloro-2-quinoxalyloxy)phenoxy]propionic acid and 8.8 g of N,N-dimethylformamide were charged into a flask and stirred at room temperature. Then, 1.1 g (0.08 mol) of potassium carbonate and 1.3 g (0.011 mol) of tetrahydrofurfuryl chloride were added thereto. The temperature was raised to 110° C., and the mixture was reacted for 15 hours to obtain 2.92 g (yield: 67%) of tetrahydrofurfuryl D(+)-2-[4-(6-chloro-2-quinoxalyloxy)phenoxy]propionate. The optical purity was 96%ee.

EXAMPLE 8

0.26 g of tributylamine and 12.0 g (87 mmol) of potassium carbonate were added at 60° C. to a toluene solution containing 9.83 g (29 mmol) of D(+)-2-[4-(6-chloro-2-quinoxalyloxy)phenoxy]propionic acid obtained in the same manner as in Example 1, followed by stirring for 30 minutes. Then, 14.9 g (58 mmol) of tetrahydrofurfuryl 4-toluenesulfonate was added dropwise thereto, and the mixture was reacted at 100° C. for 5 hours. After cooling, 15 g of water was added thereto, and the aqueous layer was separated and removed. The toluene layer was washed twice with 15 g of water. Then, the toluene layer was distilled, and the residue was crystallized from a solvent mixture of heptane-isopropyl ether to obtain 11 g (yield: 88%) of tetrahydrofurfuryl D(+)-2-[4-(6-chloro-2-quinoxalyloxy)phenoxy]propionate. The optical purity was 96%ee.

EXAMPLE 9

6.9 g (0.02 mol) of D(+)-2-[4-(6-chloro-2-quinoxalyloxy)phenoxy]propionic acid, 15.9 g of toluene and 4.64 g of N,N-dimethylformamide were charged into a flask, and the temperature was raised to 60° C. To this reaction solution, 8.3 g (0.06 mol) of potassium carbonate and 0.5 ml of tri-n-butylamine were further added, and 7.2 g (0.04 mol) of tetrahydrofurfuryl 2-methanesulfonate was added dropwise thereto at 60° C., followed by stirring for 2 hours. Then, the temperature was raised, and the mixture was stirred at 80° C. for 14 hours. After cooling, the reaction solution was washed three times with water. Then, toluene was distilled off under reduced pressure to obtain tetrahydrofurfuryl D(+)-2-[4-(6-chloro-2-quinoxalyloxy)phenoxy]propionate. The optical purity was 96%ee.

EXAMPLE 10

6.9 g (0.02 mol) of D(+)-2-[4-(6-chloro-2-quinoxalyloxy)phenoxy]propionic acid and 15.9 g of N,N-dimethylformamide were charged into a flask, and the temperature was raised to 60° C. To this reaction solution, 8.3 g (0.06 mol) of potassium carbonate and 0.5 ml of tri-n-butylamine were added, and further 10.9 g (0.04 mol) of isopropylidene aminoxyethyl 2-p-toluenesulfonate was added dropwise thereto at 60° C. Then, the temperature was raised and the mixture was stirred at 80° C. for 4 hours. After completion of the reaction, N,N-dimethylformamide was distilled off under reduced pressure, and toluene was added thereto. This reaction solution was washed three times with water. Then, toluene was distilled off under reduced pressure to obtain isopropylidene aminoxyethyl D(+)-2-[4-(6-chloro-2-quinoxalyloxy)phenoxy]propionate. The optical purity was 96%ee.

According to the present invention, D(+)-2-[4-(6-chloro-2-quinoxalyloxy)phenoxy]propionic acid and its ester can be produced at a high conversion in good yield without deterioration of the optical purity.

What is claimed is:

1. A process for producing D(+)-2-[4-(6-chloro-2-quinoxalyloxy)phenoxy]propionic acid, which comprises reacting an alkali metal salt of 4-(6-chloro-2-quinoxalyloxy)phenol with an alkali metal salt of L-2-chloropropionic acid in an aromatic hydrocarbon solvent in the presence of an aprotic polar solvent to obtain an alkali metal salt of D(+)-2-[4-(6-chloro-2-quinoxalyloxy)phenoxy]propionic acid, and treating it with an acid.

2. A process for producing D(+)-2-[4-(6-chloro-2-quinoxalyloxy)phenoxy]propionic acid, which comprises reacting an alkali metal salt of 4-(6-chloro-2-quinoxalyloxy)phenol with L-2-chloropropionic acid in an aromatic hydrocarbon solvent in the presence of an aprotic polar solvent and an alkali metal hydroxide to obtain an alkali metal salt of D(+)-2-[4-(6-chloro-2-quinoxalyloxy)phenoxy]propionic acid, and treating it with an acid.

3. A process for producing D(+)-2-[4-(6-chloro-2-quinoxalyloxy)phenoxy]propionic acid, which comprises reacting 4-(6-chloro-2-quinoxalyloxy)phenol with an alkali metal salt of L-2-chloropropionic acid in an aromatic hydrocarbon solvent in the presence of an aprotic polar solvent and an alkali metal hydroxide to obtain an alkali metal salt of D(+)-2-[4-(6-chloro-2-quinoxalyloxy)phenoxy]propionic acid, and treating it with an acid.

4. The process according to claim 1, wherein the alkali metal salt of 4-(6-chloro-2-quinoxalyloxy)phenol is produced by reacting 2,6-dichloroquinoxaline with hydroquinone in an aromatic hydrocarbon solvent in the presence of an alkali metal hydroxide and an aprotic polar solvent.

5. The process according to any one of claim 1, wherein N,N-dimethylformamide is used as the aprotic polar solvent.

6. The process according to any one of claim 1, wherein toluene or benzene is used as the aromatic hydrocarbon solvent.

7. The process according to claim 2, wherein the reaction is carried out while removing formed water.

8. A process which comprises the following steps:

(a) reacting an alkali metal salt of 4-(6-chloro-2-quinoxalyloxy)phenol with an alkali metal salt of L-2-chloropropionic acid in an aromatic hydrocarbon solvent in the presence of an aprotic polar solvent; or reacting an alkali metal salt of 4-(6-chloro-2-quinoxalyloxy)phenol with L-2-chloropropionic acid in an aromatic hydrocarbon solvent in the presence of an aprotic polar solvent and an alkali metal hydroxide; or reacting 4-(6-chloro-2-quinoxalyloxy)phenol with an alkali metal salt of L-2-chloropropionic acid in an aromatic hydrocarbon solvent in the presence of an aprotic polar solvent and an alkali metal hydroxide;

(b) treating the product from step (a) with an acid to obtain D(+)-2-[4-(6-chloro-2-quinoxalyloxy)phenoxy]propionic acid; and (c) esterifying the acid from step (b) to obtain ethyl D(+)-2-[4-(6-chloro-2-quinoxalyloxy)phenoxy]propionate or tetrahydrofurfuryl D(+)-2-[4-(6-chloro-2-quinoxalyloxy)phenoxy]propionate or isopropylidene aminoxyethyl D(+)-2-[4-(6-chloro-2-quinoxalyloxy)phenoxy]propionate.

9. The process according to claim 8, wherein tributylamine is used as the tertiary amine.

10. A process for producing ethyl D(+)-2-[4-(6-chloro-2-quinoxalyloxy)phenoxy]propionate which comprises esterifying D(+)-2-[4-(6-chloro-2-quinoxalyloxy)phenoxy]propionic acid obtained by the process of claim 1.

11. A process for producing ethyl D(+)-2-[4-(6-chloro-2-quinoxalyloxy)phenoxy]propionate, which comprises reacting D(+)-2-[4-(6-chloro-2-quinoxalyloxy)phenoxy] propionic acid obtained by the process of claim 1, with diethyl sulfate in the presence of a tertiary amine and a base.

12. A process for producing tetrahydrofurfuryl D(+)-2-[4 (6-chloro-2-quinoxalyloxy)phenoxy]propionate which comprises esterifying D(+)-2-[4-(6-chloro-2-quinoxalyloxy) phenoxy]propionic acid obtained by the process of claim 1.

13. A process for producing isopropylidene aminoxyethyl D(+)-2-[4-(6-chloro-2-quinoxalyloxy)phenoxy]propionate which comprises D(+)-2-[4-(6-chloro-2-quinoxalyloxy) phenoxy]propionic acid obtained by the process of claim 1.

14. The process according to claim 2, wherein the alkali metal salt of 4-(6-chloro-2-quinoxalyloxy)phenol is produced by reacting 2,6-dichloroquinoxaline with hydroquinone in an aromatic hydrocarbon solvent in the presence of an alkali metal hydroxide and an aprotic polar solvent.

15. The process according to claim 2, wherein N,N-dimethylformamide is used as the aprotic polar solvent.

16. The process according to claim 3, wherein N,N-dimethylformamide is used as the aprotic polar solvent.

17. The process according to claim 2, wherein toluene or benzene is used as the aromatic hydrocarbon solvent.

18. The process according to claim 3, wherein toluene or benzene is used as the aromatic hydrocarbon solvent.

19. The process according to claim 3, wherein the reaction is carried out while removing formed water.

20. A process for producing ethyl D(+)-2-[4-(6-chloro-2-quinoxalyloxy)phenoxy]propionate which comprises esterifying D(+)-2-[4-(6-chloro-2-quinoxalyloxy)phenoxy] propionic acid obtained by the process of claim 2.

21. A process for producing ethyl D(+)-2-[4-(6-chloro-2-quinoxalyloxy)phenoxy]propionate, which comprises reacting D(+)-2-[4-(6-chloro-2-quinoxalyloxy)phenoxy] propionic acid obtained by the process of claim 2, with diethyl sulfate in the presence of a tertiary amine and a base.

22. A process for producing tetrahydrofurfuryl D(+)-2-[4 (6-chloro-2-quinoxalyloxy)phenoxy]propionate which comprises esterifying D(+)-2-[4-(6-chloro-2-quinoxalyloxy) phenoxy]propionic acid obtained by the process of claim 2.

23. A process for producing isopropylidene aminoxyethyl D(+)-2-[4-(6-chloro-2-quinoxalyloxy)phenoxy]propionate which comprises esterifying D(+)-2-[4-(6-chloro-2-quinoxalyloxy)phenoxy]propionic acid obtained by the process of claim 2.

24. A process for producing ethyl D(+)-2-[4-(6-chloro-2-quinoxalyloxy)phenoxy]propionate which comprises esterifying D(+)-2-[4-(6-chloro-2-quinoxalyloxy)phenoxy] propionic acid obtained by the process of claim 3.

25. A process for producing ethyl D(+)-2-[4-(6-chloro-2-quinoxalyloxy)phenoxy]propionate, which comprises reacting D(+)-2-[4-(6-chloro-2-quinoxalyloxy)phenoxy] propionic acid obtained by the process of claim 3, with diethyl sulfate in the presence of a tertiary amine and a base.

26. A process for producing tetrahydrofurfuryl D(+)-2-[4 (6-chloro-2-quinoxalyloxy)phenoxy]propionate which comprises esterifying D(+)-2-[4-(6-chloro-2-quinoxalyloxy) phenoxy]propionic acid obtained by the process of claim 3.

27. A process for producing isopropylidene aminoxyethyl D(+)-2-[4-(6-chloro-2-quinoxalyloxy)phenoxy]propionate which comprises esterifying D(+)-2-[4-(6-chloro-2-quinoxalyloxy)phenoxy]propionic acid obtained by the process of claim 3.

\* \* \* \* \*